Figure 1:
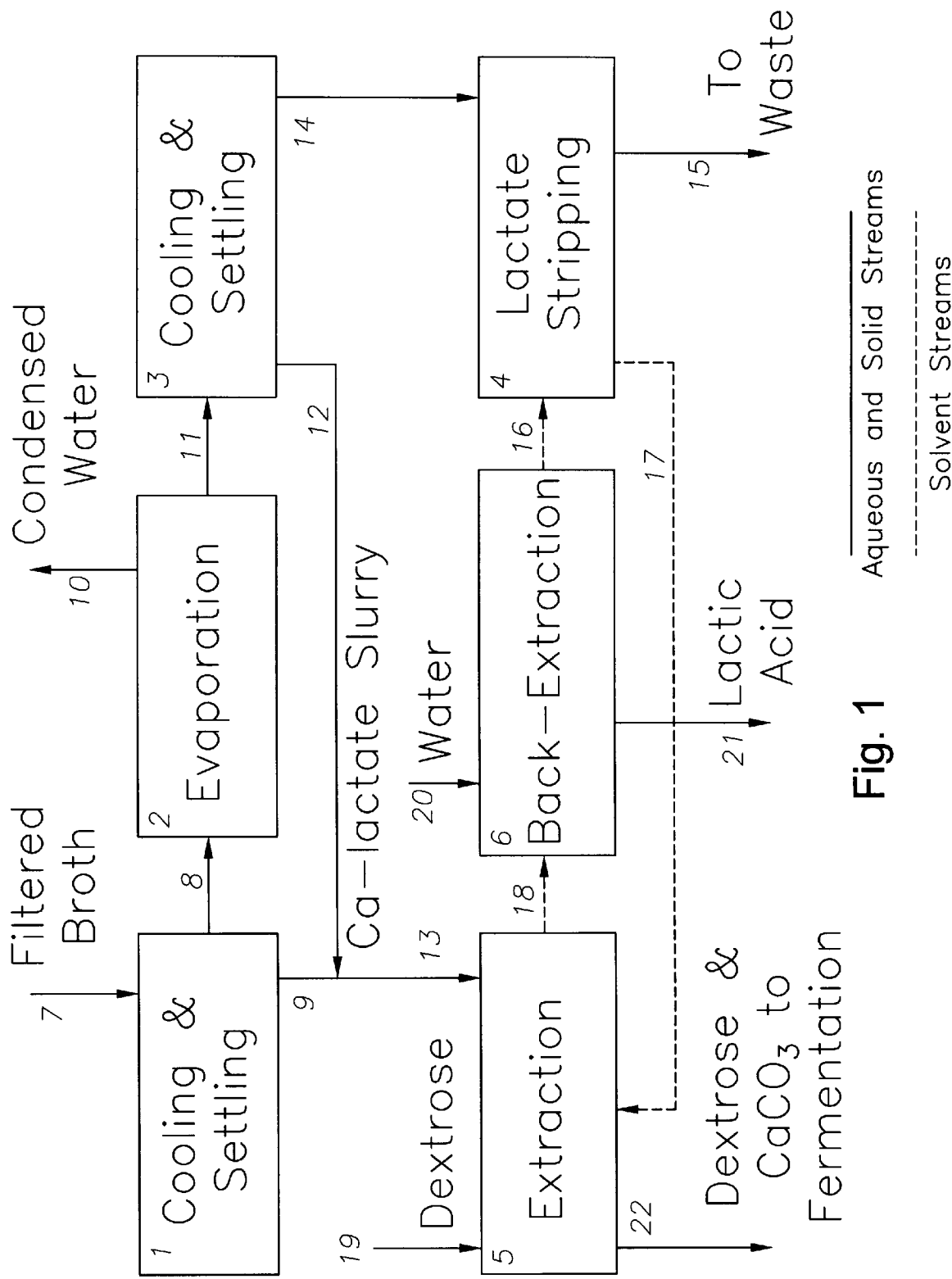

United States Patent [19]

Baniel

[11] Patent Number: 5,959,144
[45] Date of Patent: Sep. 28, 1999

[54] PROCESS FOR THE RECOVERY OF LACTIC ACID

[75] Inventor: Avraham Baniel, Jerusalem, Israel

[73] Assignee: A. E. Staley Manufacturing Company, Decatur, Ill.

[21] Appl. No.: 09/103,845

[22] Filed: Jun. 24, 1998

[30] Foreign Application Priority Data

Jun. 30, 1997 [IL] Israel ......................................... 121207

[51] Int. Cl.$^6$ .................................................... C07C 51/42
[52] U.S. Cl. ........................................... 562/580; 562/589
[58] Field of Search ............................................. 562/580

[56] References Cited

U.S. PATENT DOCUMENTS

| | | | |
|---|---|---|---|
| 5,136,057 | 8/1992 | Bhatia | 562/580 |
| 5,510,526 | 4/1996 | Baniel et al. | 562/580 |
| 5,773,653 | 6/1998 | Baniel | 562/580 |
| 5,780,276 | 7/1998 | Baniel | 562/580 |
| 5,780,678 | 7/1998 | Baniel et al. | 562/580 |
| 5,831,122 | 11/1998 | Eyal | 562/580 |

*Primary Examiner*—Paul J. Killos
*Attorney, Agent, or Firm*—Williams, Morgan & Amerson

[57] ABSTRACT

The invention provides a process for the recovery of lactic acid from an aqueous liquor containing water and calcium lactate, comprising the extraction step of combining the lactate aqueous liquor with an extractant containing at least one water immiscible amine having a total of at least 18 carbon atoms in the presence of carbon dioxide to form an aqueous phase and an organic phase containing extracted lactic acid and the extractant and separating lactic acid from the organic phase, characterized in that a carbohydrate is added to the aqueous liquor, the carbohydrate being present in the aqueous liquor at a weight concentration of at least 10% of the water content thereof.

5 Claims, 1 Drawing Sheet

PROCESS FOR THE RECOVERY OF LACTIC ACID

The present invention relates to a process for the recovery of lactic acid. More particularly the present invention relates to the production, preparation and recovery of lactic acid from an aqueous liquor containing calcium lactate.

As is known and as stated in U.S. Pat. No. 5,510,526 the full teachings of which are incorporated herein by reference, lactic acid has long been used as a food additive and in various chemical and pharmaceutical applications. More recently, lactic acid has been used in the making of biodegradable polymers both as a replacement for present plastic materials as well as various new uses where biodegradability is needed or desired. Accordingly, there is an ever increasing demand for lactic acid, the present invention aims at meeting this demand by providing an efficient and environmentally friendly process for producing lactic acid which avoids the consumption of bases and acids and substantially reduces, if not eliminates, the formation of waste or by-product salts.

Calcium lactate has been for many years and still is the primary, fermentation produced, material for the manufacture of lactic acid. The traditional method of effecting the transformation of calcium lactate to lactic acid can be summarized by the formula $$CaL_2 + H_2SO_4 = CaSO_4 + 2HL \qquad (1)$$

wherein L stands for the lactate anion $CH_3CHOHCOO$.

This process, however, has many disadvantages, the most obvious of which is the formation of calcium sulfate representing both reagent consumption and a disposal problem.

The interest of replacing sulfuric acid $H_2SO_4$ by carbonic acid $H_2CO_3$ (i.e. $CO_2+H_2O$) has been recognized for many years. Such a replacement is summarized by the formula $$CaL_2 + H_2O + CO_2 = CaCO_3 + 2HL \qquad (2)$$

The calcium carbonate could be recycled to fermentation where $CO_2$ is liberated and could be recovered for reuse. In such a prospective process no reagents are wasted and no solid waste that needs disposal is produced.

Various attempts to achieve a commercially viable process based on reaction (2) are on record. The most recent two are Baniel et al. U.S. Pat. No. 5,510,526 and Miller et al. Ind. Eng. Chem. Res. 1995 36 pp 1156–1162. These publications extensively review the relevant prior art so that for the purposes of defining the uniqueness of the present invention reference will be made to these two publications only.

Referring now to the teachings of these references, whereas reaction (1) representing the traditional process goes fully to the right due to the acid strength of $H_2SO_4$ relative to the acid strength of HL, reaction (2) representing the desirable alternate process proceeds only infinitesimally to the right due to the weakness of carbonic acid $H_2CO_3$ compared to HL. All attempts of achieving reaction (2) were based on shifting the reaction from left to right by playing on two factors: (a) providing a solvent phase that will capture lactic acid and remove it from the aqueous phase where the reaction takes place and (b) apply $CO_2$ pressure so as to increase the driving force provided by the carbonic acid. This combination of reaction and Solvent Extraction results in the formation of solid calcium carbonate and in lactic acid held in solvent. The latter being an amine based solvent, one can consider that the lactic acid is held as amine-lactate in the solvent phase from which it need be recovered.

Miller et al. tested amine-based solvent compositions of great basicity in attempts to shift maximally reaction (2) in the desired direction. They conclude: "We showed that 1-octanol/Amberlite LA-2 is capable of extracting lactic acid from aqueous solutions of calcium lactate in the presence of carbon dioxide at pressures as low as 1 bar, and of simultaneously precipitating calcium carbonate . . . However, the capacity of the extractant is low by comparison to industrial commodity-chemical solvent extraction systems. Also, free lactic acid is difficult to recover from the amine-lactic acid complex." One notes that Amberlite LA-2 is a secondary amine of greater base strength than most tertiary amines such as tridodecylamine used in industrial Solvent Extraction.

U.S. Pat. No. 5,510,526 compares reaction (2) with calcium lactate to similar reactions with sodium lactate and potassium lactate using amine based solvents that allow the recovery of the lactic acid as free lactic acid by means of back-extraction with water (Example 4, p.11). Experiments 1 to 4 of this Example which relate to calcium lactate provide for the computation of the actual concentrations of lactate in the solvent phase. These are: 0.01; 0.05; 0.07; 0.08 moles lactic acid per 1 kg solvent for $CO_2$ gauge pressures of 0, 150, 220, 300 psi respectively. These very low concentrations contrast with concentrations as high as 0.6 moles/Kg of experiment 10 done with sodium lactate at 300 psi and indeed U.S. Pat. No. 5,510,526 claims the recovery of lactic acid from sodium lactate as the preferred embodiment of the invention. One notes that this experiment 10 was done with saturated sodium lactate of about 38% and that the experiments 1 to 4 with calcium lactate were also done with a saturated solution of this salt which is approximately 6% at the temperature of 25° C. at which these experiments were run.

Miller established clearly that, as expected on thermodynamic considerations, increasing $CO_2$ pressure increases conversion of calcium lactate the effect leveling off at 15 to 20 bars (approximately 224 to 300 psi) and similar results are evident from U.S. Pat. No. 5,510,526. Miller also established that amine strength combined with $CO_2$ pressure does not provide for conversions of practical significance. U.S. Pat. No. 5,510,526 established that with sodium lactate of high concentrations relatively high conversions are attainable. By implication, the acceptance of impracticality of recovering lactic acid from calcium lactate was due to the low solubility of calcium lactate compared to sodium lactate. To test this conclusion experiments 1 and 2 of Example 4 page 11 in U.S. Pat. No. 5,510,526 were repeated with the difference that the amount of lactate present was doubled. The excess of calcium lactate over solubility formed a slurry. This procedure ensured that saturation to calcium lactate was maintained. The solvent phase was analyzed for lactate. The results are tabulated below:

| | equivalents/Kg solvent | |
| --- | --- | --- |
| experiment no. | U.S. Pat. No. 5,510,526 | with excess $CaL_2$ |
| No. 1, zero pressure | 0.01 | 0.015 |
| No. 2, 150 psi | 0.05 | 0.08 |

One notes that maintaining the concentration of calcium lactate at the maximum allowed by temperature improves somewhat the concentration in the extractant phase but not to a significant extent. Thus the teachings of these publications do not provide for a practical process for recovering lactic acid from calcium lactate.

After much further research and development it has now been discovered that the addition of carbohydrates such as dextrose or sucrose to an aqueous slurry of calcium lactate greatly enhances the extractibility of lactic acid by amine based extractants, all other conditions remaining unchanged.

Thus, according to the present invention there is now provided a process for the recovery of lactic acid from an aqueous liquor containing water and calcium lactate, comprising the extraction step of combining said lactate aqueous liquor with an extractant containing at least one water immiscible amine having a total of at least 18 carbon atoms in the presence of carbon dioxide to form an aqueous phase and an organic phase containing extracted lactic acid and said extractant and separating lactic acid from said organic phase, characterized in that a carbohydrate is added to said aqueous liquor, said carbohydrate being present in said aqueous liquor at a weight concentration of at least 10% of the water content thereof.

It will thus be realized that the present invention constitutes a modification and improvement on the process described in U.S. Pat. No. 5,510,526 and as stated the relevant teachings of said patent especially with regard to reactants and reaction conditions are incorporated herein by reference, although the present invention is not limited to the features of said patent and can be applied in other systems and variations thereof as well.

While the invention will now be described in connection with certain preferred embodiments in the following example so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

100 grs. calcium lactate pentahydrate ($CaL_2.5H_2O$) were added to 47 grs water and 18 grs dextrose and were mixed in an autoclave to form a slurry. 2500 grs of solvent were added to the autoclave which was purged by a stream of $CO_2$, put under a pressure of 75 psi and agitated for 1 hr at 20° C. The solvent was composed of Trycaprylylamine 48%, n-octanol 30% and a non-aromatic hydrocarbon diluent 22%—a composition typical of those given in U.S. Pat. No. 5,510,526 and in extraction of carboxylic acids by amine-based solvents in general. Agitation was stopped and the contents of the autoclave were allowed to settle and were separated and depressurized. A clear organic phase was obtained and an aqueous slurry which was noticeably more fluid than the initial slurry. The solvent phase weighed 2580 grs and contained 1.9% lactic acid or 0.21 equivalents/Kg. The extracted acid amounted to 49 grs out of the total of 58.4 contained in the calcium lactate i.e. 84% recovery. The solids in the aqueous slurry were separated by filtration, washed by water and dried. They weighed 25.5 grs and assayed 95% $CaCO_3$.

This example clearly establishes that the presence of dextrose brings about a radical change to prior art. In fact the concentration of lactic acid obtained in the solvent is larger by a full order of magnitude compared to concentrations obtainable from calcium lactate solutions or slurries under comparable conditions.

Nor is the effect specific to dextrose. In a test identical to Example 1 except that the dextrose was replaced by an equal amount of sucrose—the results obtained were practically indistinguishable.

It will be obvious to engineers that practice Solvent Extraction that there is extensive room in which the system calcium lactate-carbohydrates-solvent lends itself to optimization by conventional means and reference to existing art with respect to carboxylic acids in general and lactic acid in particular. Such are counter-current steps (as in the preferred embodiment of U.S. Pat. No. 5,510,526), $CO_2$ pressure, solvent composition etc. and need not be expanded on in the present application.

In an especially preferred embodiment of the present invention there is used a calcium lactate containing fermentation broth rather than the pure calcium lactate used in Example 1. This is achieved by effecting the extraction of the bulk of lactic acid from a slurry of calcium lactate derived from one fermentation step to which part or all of the carbohydrate feed of the next fermentation is added and sending to this next fermentation the slurry of the $CaCO_3$ (formed by the extraction) in the solution of the carbohydrate feed, this solution retaining also any residual unreacted calcium lactate.

The practice of U.S. Pat. No. 5,510,526 requires the evaporation of the sodium lactate broth obtained by fermentation to recover a saturated solution of some 35% suitable for extraction. A similar evaporation could be used in the present case with calcium lactate broths. However such evaporation has the disadvantage of concentrating all of the impurities present in the broth thereby increasing any tendencies for co-extraction with lactic acid.

As described hereinafter, in a further preferred embodiment of the present invention this bulk evaporation is avoided thereby resulting in efficient evacuation of impurities, energy savings and process advantages explained further below.

The solubility of calcium lactate changes sharply with temperature. Fermentations are run at relatively high temperatures that provide for calcium lactate solubility of some 17%; by cooling the filtered broth to 25° C. at which only about 6% calcium lactate are soluble, about 65% of the lactate precipitates and is easily collected in a 30%–50% solids slurry containing some 2% to 5% lactate in solution so that the slurry accounts for some 70% of lactate in the broth. The supernatant clear liquor is partially evaporated and cooled and the slurry separated rejoins the first, the combined slurry reaching a lactate content dependent on the extent of evaporation. Evaporating 50% of the water will provide a slurry of some 90% of total lactate and a residual liquor containing some 35% of the water in the initial broth and the remainder of the lactate. This remainder is fully recovered by contacting in presence of $CO_2$ with fresh solvent prior to its use in the main extraction.

In order that the invention and preferred embodiments thereof may be better understood and appreciated reference will now be made to the accompanying figure which is a flow diagram of preferred operational steps of the present invention.

Referring to said figure there is seen that in step (1) filtered fermentation broth (7) is fed continuously in a step in which it is cooled to 20° C./30° C. whereby solid calcium lactate separates, allowed to settle and is withdrawn as a slurry (9) of solid contents in the range of 30% to 50%. Solids/liquid separation need not be complete, the supernatant liquid stream (8) can be allowed to contain fine solids that do not settle rapidly by virtue of the next recovery step (2). This allowance renders step (1) easy and inexpensive.

In step (2) the supernatant (8) exiting step (1) is heated and partially evaporated. Since the solubility of calcium lactate increases sharply with temperature, this is a standard non-problematic step allowing for easy control and adjustment of evaporation to any predetermined level. The evaporated water (10) is condensed and the concentrate (11) is sent to step (3).

Step (3) is identical to (1) and is carried out in a reactor which is about one half of the size of the reactor used in step (1). The calcium lactate slurry (12) recovered by settling rejoins slurry stream (9) to form (13) which is the feed to extraction step (5); the supernatant (14) that still contains about 5% to 10% of the lactate in feed (7) reports to Lactate Stripping step (4).

In step (4) the residual aqueous stream (14) is stripped of the lactate it contains by extraction with the full stream of solvent (16). Since this stream coming from back-extraction is free of lactic acid and has the capacity to extract the full amount of lactate in feed (7) it presents a very large excess with respect to the lactate contained in (14). Consequently, under low or even zero pressure of $CO_2$ and 2 to 4 counter-current stages all of the lactate in (14) reports to the solvent stream (17). The aqueous residue (15) containing impurities and only traces of lactate reports to waste treatment. Optionally, as a way to better utilization of the large excess capacity available in stream (16) it can be split into two: (16a) and (16b) (not indicated on the diagram) using (16a) for step (4) and sending HL-containing (16a) and HL-free (16b) to two selected points in the counter-current liquid-liquid-contacting battery of Extraction step (5).

In step (5) calcium lactate slurry (13) is mixed with dextrose (19) to form the aqueous feed to extraction. Actually "dextrose" stands for any carbohydrate or mixture of carbohydrates actually in use for lactic fermentation. But for the sake of simplicity of presentation "dextrose" will be used to refer to carbohydrates feed generally.

The amount of dextrose applied is calculated to provide 25 grs to 65 grs per 100 grs of water present in slurry (13). The amount of water in the slurry that needs be considered in this calculation consists of water accompanying the dextrose (if any); water present in the slurry and the water of crystallization of the calcium lactate. The reason for the last item is that as $CaL_2.5H_2O$ converts to $CaCO_3$, five mols of $H_2O$ are liberated. The amount of dextrose defined by the foregoing is naturally available as a consequence of the fact that the amount of dextrose needed for each weight unit of lactic acid exceeds the ratio 1:1, this ratio representing a theoretical, 100% conversion that does not consider consumption for the microorganism biomass. A simple calculation indicates that the amount of dextrose available is sufficient to satisfy dextrose concentration requirements even if this dextrose used is actually a syrup of 50% by weight.

The extraction itself which takes place is preferably counter-current and under $CO_2$ pressure as in the prior art. If stream (16) is not split in two, then (17) enters the counter-current solvent extraction battery at the opposite end to the aqueous feed. If (16) is split into (16a) and (16b) then (16b), which is free of HL, enters at the opposite end and (16a) which becomes (17) enters at a mid-point that fits its level of loading with HL.

The extraction of lactate in step (5) could aim at completeness, but is better left incomplete with 5% to 15% reporting to the aqueous raffinate stream (22). This provides for fewer contacting stages and for maximizing HL concentration in the Extract 18 which in turn provides for high concentrations of product lactic acid (21).

Stream 22 returns to fermentation unreacted calcium lactate plus $CaCO_3$ equivalent to the reacted calcium lactate thereby preventing lactate losses and keeping all of the calcium requirements of fermentation in closed recycle. Handling of $CaCO_3$ is restricted to minor make-up quantities. Stream (22) also contains part or all of the dextrose requirements of fermentation.

Back-extraction (6) is a conventional counter-current liquid-liquid-contacting step. Since strong basic extractants such as specified in Example 1 are desirable, the back-extraction may be preferably run at temperatures above 100° C., but, for reasons of stability, preferably not exceeding 150° C., in order to secure satisfactory concentrations of HL in product stream (21). This will obviously require operating under pressure.

In other preferred embodiment in the present invention, instead of using octanol, or other organic compounds of similar number carbon atoms which render them water-insoluble, as an enhancer of basicity, there are used extractants which contain lower molecular weight enhancers such as nPrOH or nBuOH and there is applied a technology that obviates the need for high temperatures as described in: "Recovery Of Carboxylic Acid From Organic Solution That Contains An Amine And An Extraction Enhancer", PCT/EP95/02399 and PCT/EP95/01889. The application of this technology has the added advantage that it permits the use of solvents of higher base strengths than would be otherwise possible.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of lactic acid from an aqueous liquor containing water and calcium lactate, comprising the extraction step of combining said lactate aqueous liquor with an extractant containing at least one water immiscible amine having a total of at least 18 carbon atoms in the presence of carbon dioxide to form an aqueous phase and an organic phase containing extracted lactic acid and said extractant and separating lactic acid from said organic phase, characterized in that a carbohydrate is added to said aqueous liquor, said carbohydrate being present in said aqueous liquor at a weight concentration of at least 10% of the water content thereof.

2. A process according to claim 1 wherein said carbohydrate is selected from the group consisting of dextrose and sucrose.

3. A process according to claim 1 wherein said aqueous liquor is obtained from a calcium lactate containing fermentation broth.

4. A process according to claim 1 wherein said amine is a water-immiscible trialkyl amine.

5. A process according to claim 1 wherein the extracted lactic acid is recovered by back-extraction of the organic phase with water.

* * * * *